(12) United States Patent
Benayon

(10) Patent No.: US 11,694,531 B2
(45) Date of Patent: Jul. 4, 2023

(54) SMART GAS MONITORING DEVICE

(71) Applicant: Yesukai Fernand Azevedo Benayon, Brazoria, TX (US)

(72) Inventor: Yesukai Fernand Azevedo Benayon, Brazoria, TX (US)

( * ) Notice: Subject to any disclaimer, the term of this patent is extended or adjusted under 35 U.S.C. 154(b) by 259 days.

(21) Appl. No.: 17/210,090

(22) Filed: Mar. 23, 2021

(65) Prior Publication Data
US 2022/0309894 A1 Sep. 29, 2022

(51) Int. Cl.
*G08B 17/103* (2006.01)
*G01N 33/00* (2006.01)
*G05B 19/048* (2006.01)
*G01N 21/61* (2006.01)

(52) U.S. Cl.
CPC ........... *G08B 17/103* (2013.01); *G01N 21/61* (2013.01); *G01N 33/0004* (2013.01); *G05B 19/048* (2013.01); *G05B 2219/2642* (2013.01)

(58) Field of Classification Search
CPC ...... G08B 17/103; G08B 21/14; G01N 21/61; G01N 33/0004; G05B 19/048; G05B 2219/2642; G05B 19/042
See application file for complete search history.

(56) References Cited

U.S. PATENT DOCUMENTS

2022/0336171 A1* 10/2022 Jin ..................... G01R 31/3271
2022/0347423 A1* 11/2022 Babbage ........... A61M 16/0066

* cited by examiner

*Primary Examiner* — Michael C Zarroli

(57) ABSTRACT

The present invention relates to a smart gas monitoring system configured at a confined space. The smart gas monitoring system measures concentration of hazardous gases at regular intervals and generates an alarm if concentration of a gas increases beyond a pre-defined value. The smart gas monitoring system also generates an alert to a number of laborers on their electronic devices, along with measuring their health conditions.

21 Claims, 6 Drawing Sheets

SMART GAS MONITORING DEVICE

FIELD OF INVENTION

The present invention generally relates to systems and methods for providing real time monitoring and notification of hazardous gases in a confined space. More specifically, the invention provides a smart gas monitoring device for identifying concentration of the hazardous gases in the confined space and generating alerts to laborers on their electronic device.

BACKGROUND OF THE INVENTION

Monitoring the concentration of gases, especially the hazardous ones in confined spaces such as wells, tanks or bore wells becomes a requirement due to the potential problems these gases can cause to the health of the laborers working inside these confined spaces. Exposure to poisonous gases like carbon dioxide and hydrogen disulphide can cause severe headaches and even dizziness. High concentrations of these gases can cause unconsciousness and can even result in death. Thus, for the safety of the workers, a gas monitoring system capable of detecting and measuring the concentration of toxic gases is of utmost importance in confined spaces.

Mostly the gas monitors are installed in desolated or confined spaces. Theses gas monitors than generate an alarm in case any of the hazardous gases are present in a concentration that is higher than the set threshold value. One such example is U.S. Pat. No. 9,612,195 assigned to Bert Friedman discloses a gas detector for monitoring gases in confined spaces. The gas detector includes a plurality of sensors, an alarm system to warn the workers when the concentration of hazardous gases above a threshold. However, the gas detector does not consist of a camera thus making the device incapable of capturing the surroundings. So, we are unable to analyze the whole space properly.

Another U.S. Patent Application 20180330595 overcomes the limitations of the above mentioned prior art to some extent by disclosing a confined space failsafe access system that apart from having the essential components required in sensing the hazardous gases, includes a camera that monitors the condition of the workers at all times. However, there is no connection of the gas detector with a server to alert all the laborers about their vitals or about the condition of the confined space.

To overcome the shortcomings of analyzing the confined space accurately and precisely, another U.S. patent application 20200150077 assigned to Chuan-Bao Wang discloses a portable electrochemical or combustible lower explosive limit gas sensing apparatus. The gas sensing apparatus includes a housing comprising at least one exterior surface and an interior space. The invention also provides a processing unit is disposed in the interior space of the housing and is in electrical communication with the electrochemical gas sensor or the combustible LEL gas sensor. Though, the application overcomes the feature of monitoring the confined location and the health of the laborer in that location and alerting the user on a portable electronic device. Still the invention lacks the provision of providing the sample of hazardous from different points at a specific location.

So there is a need of a gas monitor that monitors a confined space for the presence of hazardous gases. Moreover, analyze the vitals of the laborers and alert them when the situation of the location is inhabitable for them. The gas monitor measures the concentration of hazardous gases from different heights at a location. So, the analysis of the presence of gases is precise.

It is apparent now that numerous methods and systems are developed in the prior art that are adequate for various purposes. Furthermore, even though these inventions may be suitable for the specific purposes to which they address, accordingly, they would not be suitable for the purposes of the present invention as heretofore described. Thus, there is a need for a smart gas monitor that not only provides a live feed of the location with the details of the concentration of the gases. But also alert the user if the location turns inhabitable for the laborers.

SUMMARY OF THE INVENTION

The present invention generally relates to a system and method, generally referred to as a smart system, for monitoring a location for the presence of hazardous material. The system is for notifying presence of multiple gases in a confined space, the system is a smart gas monitor.

The object of the present invention is to provide a system to alert a user by generating one or more alert when the alarm unit is activated. The system is a smart gas monitoring device, to monitor the presence of hazardous material at a location. Further, the location is a confined space and the hazardous material is any number of hazardous gases. The smart gas monitoring device includes a camera mounted on a housing of the smart gas monitoring device, where the camera records visual at the confined space on real time. Furthermore, the camera is an infrared camera so it is functional in dark places too.

The smart gas monitoring device also includes a plurality of rechargeable batteries for powering itself. The batteries can also be replaced when needed. Moreover, pluralities of sensor are present within the housing of the gas monitoring device, where the plurality of sensors includes a first sensor and a second sensor. A first sensor coupled with an inlet port on the housing at one side, where the inlet port receives the one or more gases to be sensed by the first sensor to generate a first output and a second sensor coupled with an extension tube connected with the housing on other side. Further, the extension tube receives the one or more gases to be sensed by the second sensor to generate a second output. Furthermore, both of the first sensor and the second sensor are connected to an alarm unit.

The alarm unit includes a flashlight and an alarm to alert the user if any of the first output or the second output is greater than one or more of the threshold value set for an individual gas. The flashlight is activated based on either of the first output or the second output and start flashing a bright light with a time interval of mini seconds in the whole confined space. Similarly, the alarm is activated based on either of the first output or the second output and it alerts the user of the confined space by generating a loud noise. The alerts are generated if any of the toxic gas has crossed the set threshold value and the users or the laborers are alerted that the space is not safe for further working.

The objective of the present invention is to provide a system for notifying presence of one or more gases in a confined space. Further, the system includes a gas monitor that includes a sensing unit and an alerting unit, the system further includes a server and an electronic device to notify the users. The users are notified by generating an activated notification of an activated signal by the server and displaying the notification on the electronic device. Furthermore, the notification includes the details about the toxic gasses.

The other objective of the present invention is to provide a system for notifying presence of one or more gases in a confined space along with the vital information of the laborer working in that space. The system includes a gas monitor, a server, and an electronic device to alert the laborer. The system also includes a smart watch that all the laborers wear. The smart watch generates the vitals of the laborer wearing it along with the alerts of the gas monitor. Furthermore, the smart watch is also in communication with the electronic device to display the generated vitals of all the laborers along with the real time information of the number of hazardous gases.

Yet another objective of the present invention is to provide a system for notifying presence of one or more gases in a confined space with the live video feed of the space. The system in this case also includes a camera mounted on the gas monitor for providing the feed in real time.

The other objective of the present invention is directed to a portable fluid monitoring system, particularly to a portable fluid monitoring system used to measure fluid concentration. More particularly, to a portable gas monitoring system used to measure concentration of gasses from multiple points at a location and notify a user at a remote location. The portable fluid monitor is particularly useful in measuring gases concentration from landfill wells or ship tanks or other confined spaces.

The yet another objective of the present invention is to provide a system for generating real time video feed of the location and gas exposure. Particularly, the system can be used for evacuating the number of laborers present in that location in case of emergency. Further, the emergency is a situation of gas toxicity in that location or a decrease in the volume of oxygen in that location. The video feed in the particular case helps in locating the laborers stuck in the confined space.

These and other objects and advantages will become apparent from the following description of several illustrative embodiments of the invention as shown in the following illustrative drawings.

Other objectives and aspects of the invention will become apparent from the following detailed description, taken in conjunction with the accompanying drawings, which illustrate, by way of example, the features in accordance with embodiments of the invention.

Embodiments of the present invention may employ any or all of the exemplary aspects above. Those skilled in the art will further appreciate the above-noted features and advantages of the invention together with other important aspects thereof upon reading the detailed description that follows in conjunction with the drawings, which illustrate, by way of example, the features in accordance with embodiments of the invention. The summary is not intended to limit the scope of the invention, which is defined solely by the claims attached hereto.

BRIEF DESCRIPTION OF DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF DRAWINGS

A system for monitoring the presence of hazardous gases in a location is described. The system notifies the presence of multiple gases in a confined space, the system is a smart gas monitor. The smart gas monitor detects the presence of any hazardous gases such as hydrogen disulfide or carbon monoxide and issue an alert to a laborer present inside the confined space, thus cautioning the laborer against the increase in level of any of the hazardous gases beyond a threshold.

The device runs on a dual rechargeable battery system which houses a power monitor that indicates the current battery level of the gas monitoring unit. An LED is illuminated when the battery level goes below a certain limit.

An infrared camera placed atop the gas monitoring device is used to capture the surroundings of the laborers inside the confined space. The visuals recorded by the infrared camera can be displayed on one or more electronic devices carried by the laborers inside the confined space and the supervisor present outside the confined space. The electronic devices could be one or more of a smart watch, a mobile phone, a tablet, a laptop, and a desktop.

The interfacing of the camera, or the gas monitoring device in general with the one or more electronic devices is achieved with the help of a server. The cloud server receives information from the gas monitoring device on real-time basis, processes the received information and sends this information to the one or more electronic devices carried by the laborers and the supervisors inside or outside the confined space. Whenever the concentration of the gases goes beyond a certain threshold, the sensing unit, in conjunction with the alarm unit sends a signal to the server which is first processed and then sent to the electronic devices in the form of a notification.

Figure 1:
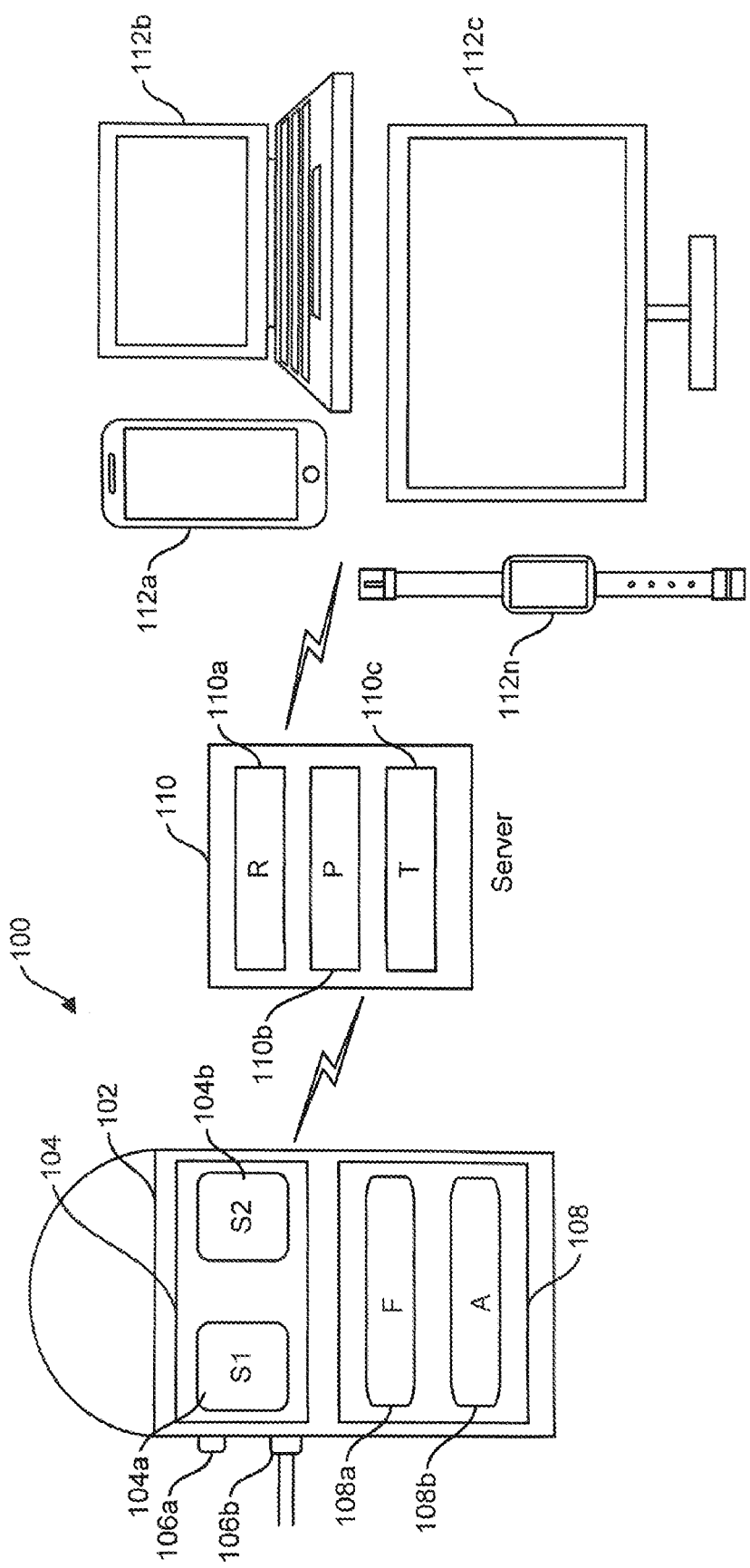
FIG. 1 illustrates a system for monitoring the presence hazardous gases in a confined space.

FIG. 1 illustrates a system 100 for monitoring the presence hazardous gases in a confined space. The system 100 includes a portable gas monitor 102, a server 110 and an electronic device 112. The gas monitor 102 is meant to be placed in a confined space for the purpose of detecting the presence of any hazardous gases through a sensing unit 104 and measuring the concentration of the said hazardous gases in the said confined space. The confined space could be a tank, a well or a bore well. The rear of the gas monitor 102 would feature a magnet for mounting it on a suitable surface such as the wall of a tank.

The gas monitor 102 would also issue an alert in case the level of oxygen goes down within the confined space and reaches a level where it becomes suffocating for the laborer. The issuance of an alert in case the concentration of hazardous gases reaches above the said threshold is achieved with the help of an alarm unit 108 placed on the housing of the gas monitor 102.

For the purpose of detecting the presence of such gases, the sensing unit 104 comprising a plurality of sensors (104a, 104b) is configured within the housing of the gas monitoring device 102. The sensing unit 104 is in communication with two inlet ports (106a, 106b) through which the hazardous gases enter the gas monitoring device and are sensed by the plurality of sensors (104a, 104b). The two inlet ports (106a, 106b) are located at different points on the housing of the gas monitoring device.

As shown in FIG. 1, one inlet port 106a is mounted on the gas monitor 102 to take a sample from the nearby space while the other is located near the bottom of the device. The other inlet port 106b located near the bottom of the gas monitor 102 is an extension tube that is routed down to the floor of the confined space to detect the presence of any hazardous gases from the lower portion of the tank or any such confined space. The sensing unit 104 is further connected to the alarm unit 108 for alerting the user when activated.

The alarm unit 108 includes two components: a sound alarm 108a and a flashlight 108b. The alarm unit 108 on activation generates the sound alarm 108a or flashes 108b a bright light on regular interval for a predefined time. The alarm unit 108 is activated when the value of the monitored gases reaches a concentration above the level of the predefined threshold value for each of the hazardous gases. Primarily, the alarm unit 108 is activated when the concentration of the hazardous gases is above the threshold value. Alternatively, a drop in the oxygen level inside the confined space also may activate the alarm unit 108.

In one embodiment, the alarm unit 108 is on activation generates a sound alarm 108a and a flashlight 108b alert. The sound alarm 108a is a high pitch alarm which is loud enough to alert the laborer inside the confined space and the supervisors monitoring the activity of the laborers outside the confined space on activation of the alarm unit. Similarly, a flashlight 108b is illuminated in a blinking pattern for a predetermined time period when the alarm unit 108 is activated.

In other embodiment, the alarm unit 108a along with the sound alarm 108a and flashlight 108b alarm also includes a signal generator. The signal generator primarily generates a signal on the basis of the output of the sensing unit 106, wherein the signal is generated when the alarm unit is activated. The activated signal is transmitted to the server 110.

The server 110 on receiving an activated signal through a receiver 110a processes the activated signal with the processor 110b to a notification. The processed notification information is transmitted to multiple electronic devices (112a-112n) with the transmitter 110c. Further, the electronic device is a smart phone (112a), a laptop (112b), a television (112c) or a smart watch (112n).

The notification information contains information about the health of the laborers present inside the confined space, concentration of various gases inside the confined space and the nature of the work being performed by the laborers inside the confined space.

This notification information can be displayed on an application configured in the electronic device (112a-112n) that the laborers and supervisors can log on to locate any laborer in trouble inside the confined space and facilitate subsequent rescue efforts. The app could permit the locations of laborers to be continuously monitored, thereby permitting any problem to be more quickly detected and a response initiated than would otherwise be possible.

Figure 2:
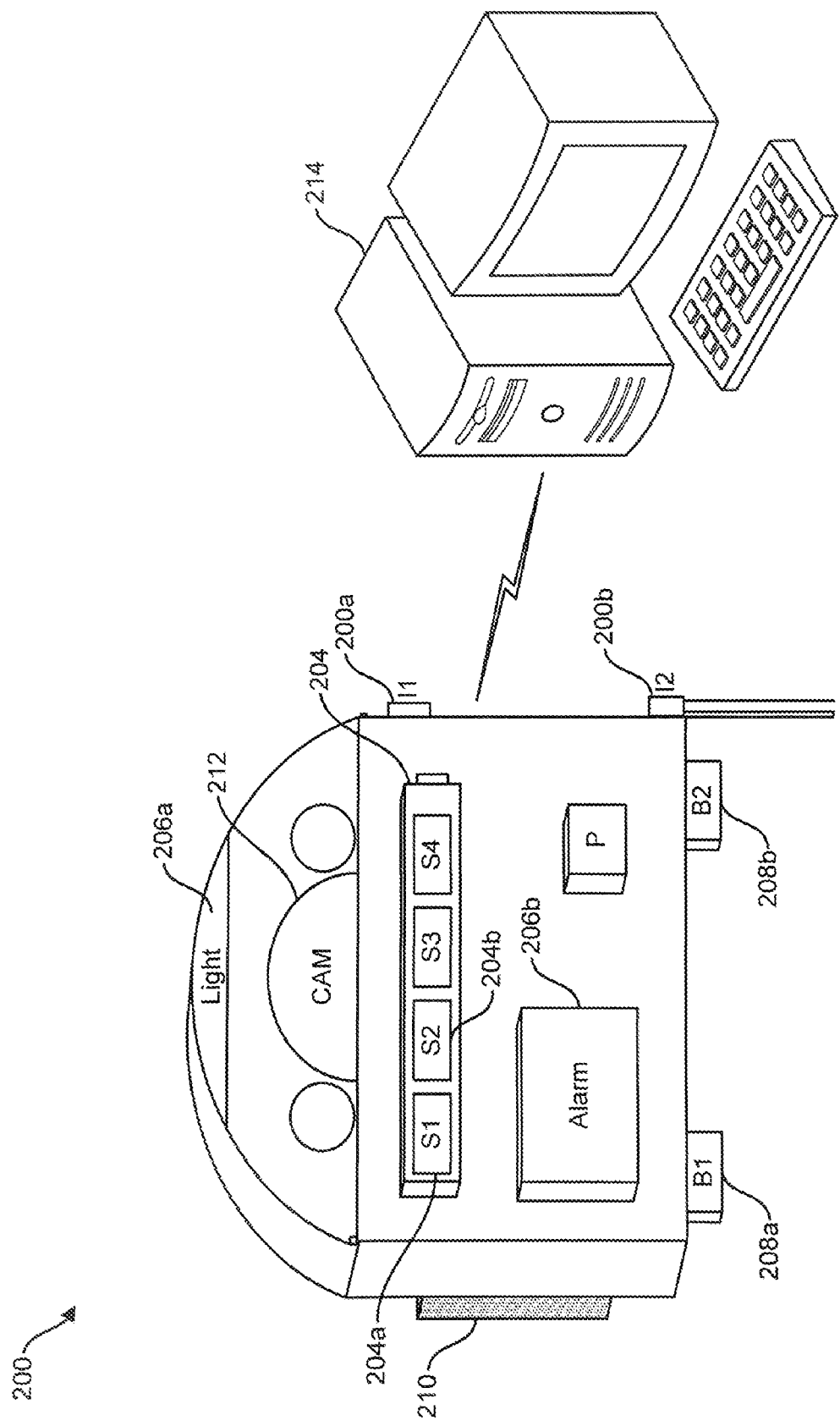
FIG. 2 Illustrate a gas monitor in communication with a server.

FIG. 2 Illustrate a gas monitor 200 in communication with server 214. The gas monitor 200 shown in the figure includes a housing made of a durable material that protects the internal components of the gas monitoring device from damage. The housing of the gas monitor 200 features a magnet 210 on its rear surface to facilitate removable connecting the device to a tank or a well as shown in FIG. 2. In an alternative embodiment, a holder made of any durable material could be affixed to the wall of the tank or a well to hold the gas monitor.

The gas monitor includes an internal power source such as a battery system 208 to power the device. The internal power source can be used to power one or more other components of the portable gas monitoring device. The internal power source can be a rechargeable and/or replaceable power source. In another embodiment, an external power source such as an external battery pack of two batteries (208a-208b), or a plug to connect into an external power source is used to power the device. The battery source houses a battery monitor which indicates the battery level when the device is in use. An LED placed on the housing is illuminated when the battery level goes below a certain level.

A sensing unit 204 is configured within the housing of the gas monitor which includes a plurality of sensors (204a-204b) to detect the presence of hazardous gases such as hydrogen disulphide, carbon monoxide or other such gases inside a confined space. The multiple sensors ((204a-204b)) monitors the concentration of gases within the confined space with the help of the first inlet 202a and the second inlet 202b with an extension tube. As both the inlets (202a-202b) are in communication with the multiple sensors (204a-204b) and provide them with the gas samples. These sensors (204a-204b) are highly sensitive and produce warning signals with the help of an alarm unit 206 placed on the housing of the device. The sensing unit 204 would generally comprise two or more than two electrochemical gas sensors (204a-204b). These sensors (204a-204b) are available as modules along with comparators. These comparators can be set for a particular threshold value of gas concentration. When the concentration of the gas exceeds this threshold, the sensing unit generates a signal which is received by the alarm unit 206 following which an alert is issued.

The sensing unit 204 is in communication with the multiple inlet ports i.e. inlet port-1 204a and inlet port-2 204b. Inlet port-1 204a takes the air sample from areas around the gas monitoring device while inlet port-2 204b which is connected to an extension tube take air samples from the bottom of the tank. The distance up to which the tube goes down the tank is roughly 5-10 feet.

The alarm unit 206 includes a flashlight 206a and a sound alarm 206b. As mentioned above, when the concentration of one or more hazardous gases increases up to a level not considered safe, the flashlight is lit. The flashlight 206a is generally an LED that emits bright light when in use. In another embodiment, any other powerful light source could be used.

A sound alarm 206b is loud enough to alert laborers working inside as well as outside the confined space is provided on the housing of the gas monitor 200. The sensing unit 204 along with the alarm unit 206 thus informs the laborers and the supervisors when the concentration of toxic gases goes beyond a set threshold or concentration of oxygen goes below a certain level. The alarm unit 206 when activated along with generating the flashlight 206a and alarm 206b, also generates a signal to be transmitted to the server 214 to alert the user.

An infrared camera 212 located at the top of the housing of the device 200 is used to capture the surroundings of the laborers working inside the confined space. The visuals of the surroundings inside the confined space are available to the supervisor to locate the laborers inside the confined space and facilitate any rescue acts in case needed.

A display screen could be installed onto the housing to display the temperature inside the confined space. Additionally, the display screen could display the concentration of gases, depth of the tank or any such confined space as an alternative embodiment.

Figure 3:
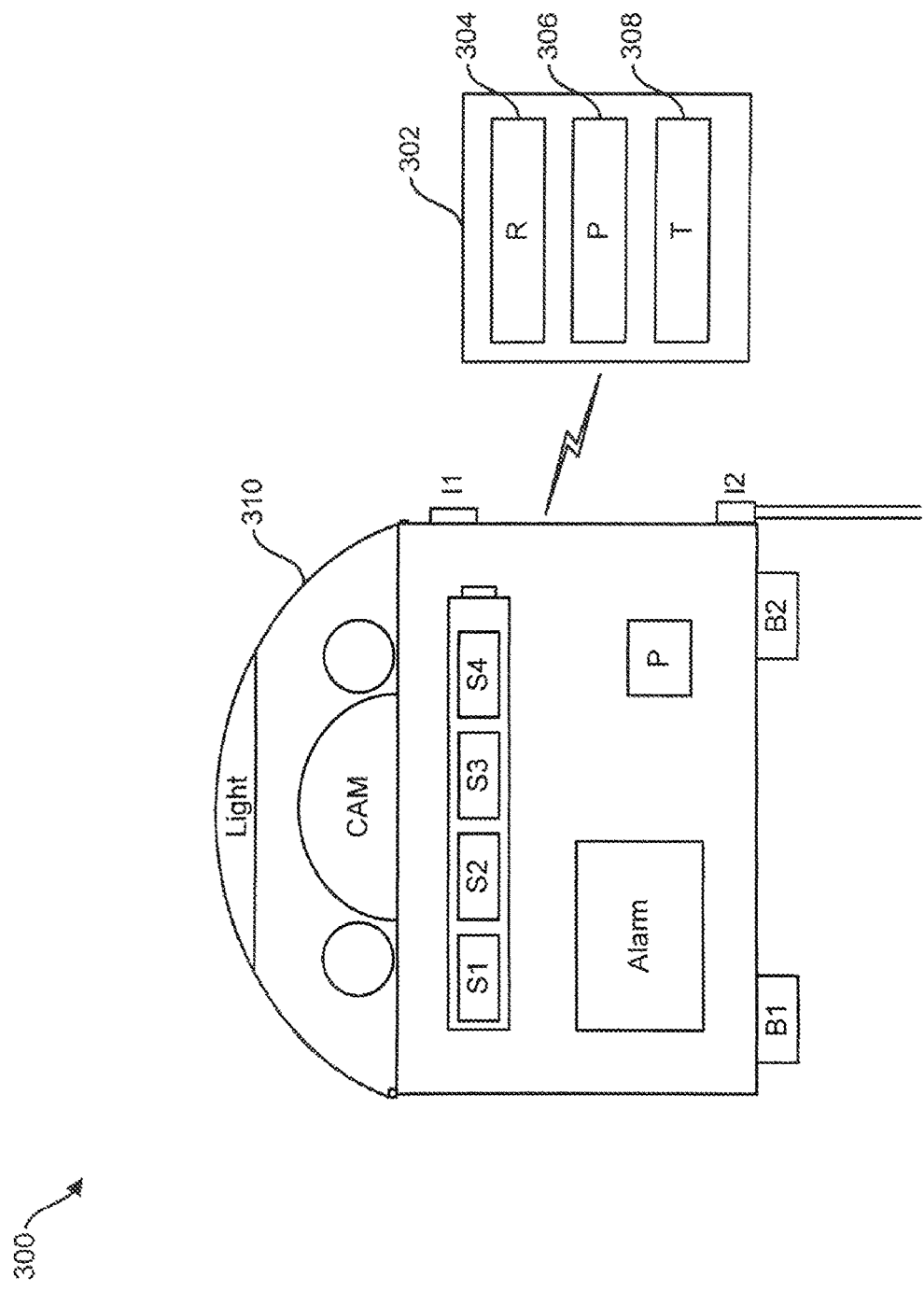
FIG. 3 Illustrate a system architecture that establishes communication between the server and the gas monitor.

FIG. 3A Illustrate a system architecture 300 that establishes communication between the server 302 and the gas monitor 310. The server 302 which exchanges information from the gas monitor 310 to the one or more electronic devices placed remotely from the gas monitor 310. The server 302 may comprise multiple servers and/or groups of servers and/or one or more cloud servers. In one preferred embodiment, the server is a cloud server. The cloud server 302 essentially consists of three parts: a receiver 304, a processing unit 306 and a transmitter 308. The server 302 is responsible for generating notification information on a real-time basis which is vital for the safety of the laborers working inside the confined space. The receiver 304 of the cloud server 302 receives an output signal from the alarm unit of the gas monitoring device which is activated when the concentration of the one or more gases inside the confined space goes above or below a set threshold value. This output has been referred to as an activation signal.

Upon reception of the activation signal, the processing unit 306 of the cloud server 302 processes this activation signal to generate a notification. The notification contains information about the concentration of various gases present inside the confined space, various health parameters of the laborers and the nature of the work being performed by the laborers inside the confined space. This notification information is sent by the transmitter 308 to one or more electronic devices placed remotely from the gas monitor 310. Other information transmitted by the server to the number of electronic devices may include live feed of the surroundings of the laborers present inside the confined space.

Figure 4A:
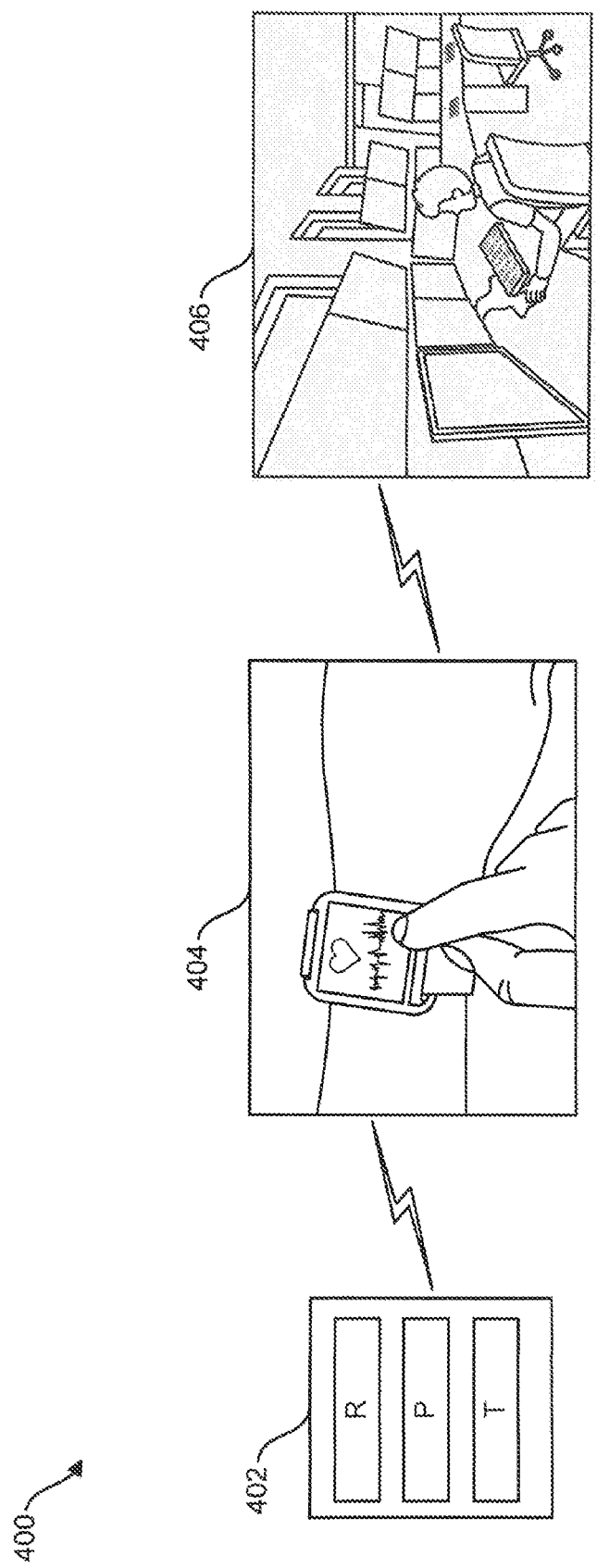
FIG. 4A Illustrates system architecture with a server communicating with a number of electronic devices.

FIG. 4 Illustrates system architecture 400 with a server 402 communicating with a number of electronic device 402-404. The connection is in between the cloud server and a plurality of smart devices that are placed remotely from the gas monitor. The FIG. 4a illustrates a communication of a server 402 with a smart watch 404 and control room 404 of the gas monitoring system 100. The server 402 achieving the communication is a cloud server. The smart watch 404 is worn by one or more laborers working inside a confined space such as a tank or a well. In an alternative embodiment, any other device that can be affixed to the body of a laborer can be used. The cloud server 402 is responsible for transmitting processed notification information to the smart watch worn by the laborers. Which upon reception of an activation signal, alerts the user by notifying him. The transmitted information also includes the vitals of the worker. The information of smart watch 402 along with the information of the gases of the confined space is transmitted to multiple electronic devices or display units in the control room 406.

Also, in communication with the cloud server is one or more display screen outside the work area for a supervisor which is a control room 406. These display screens could be present in a control room for supervisors meant to monitor the conditions inside the confined space closely via live feed and for facilitating rescue acts for laborers if needed. The cloud server also stores information such as particulars of each and every laborer, entry and exit timings of the laborers and their job description. All of this information is displayed on the display screen in a tabulated form located in a control room. In addition to this information, vital medical information related to each laborer such as their blood pressure, any past medical ailment or any allergies is also displayed. In addition to this, a video feed of the confined space is transmitted to the control room 406 on a real-time basis.

Figure 4B:
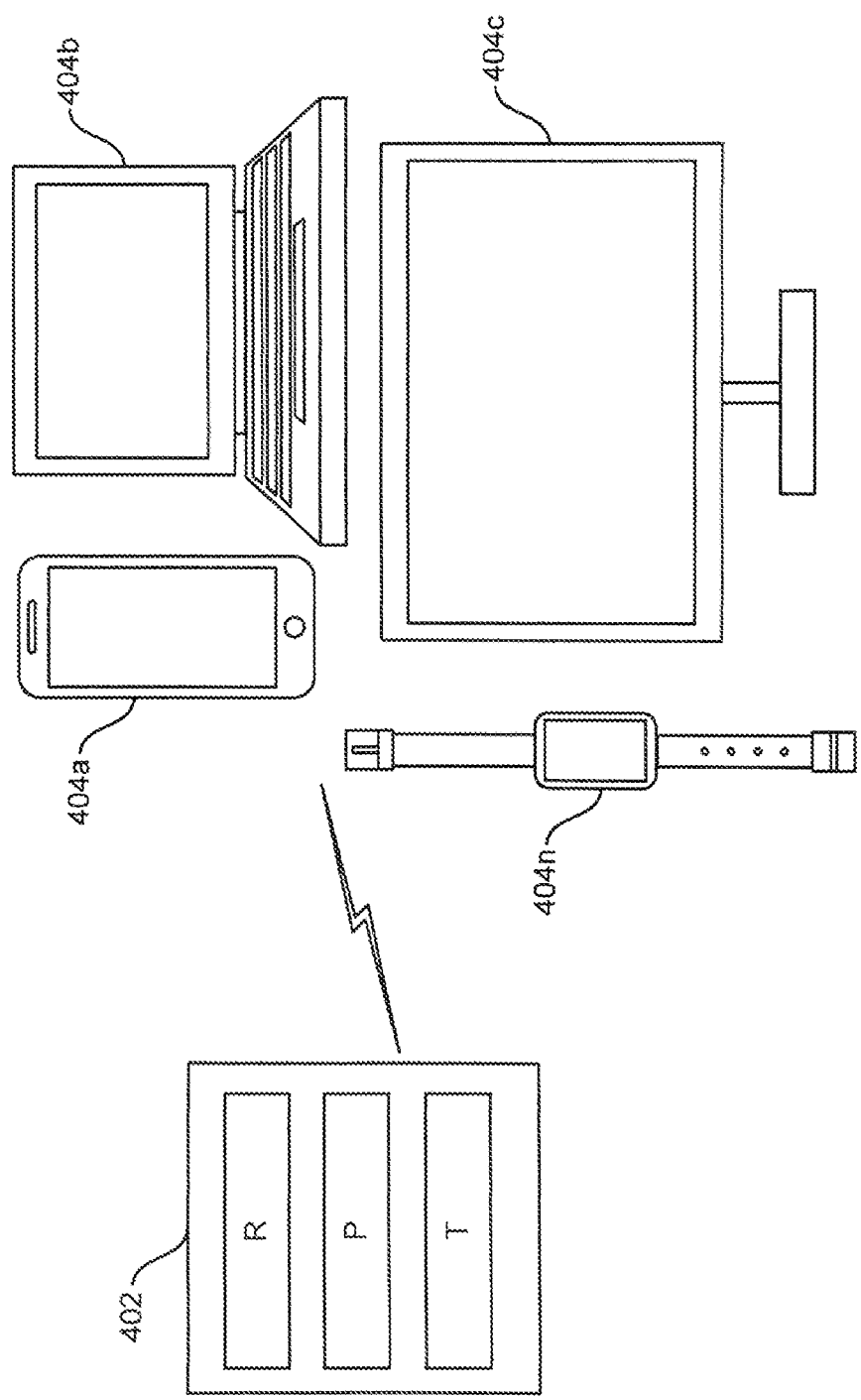
FIG. 4B illustrates a server communicating with multiple electronic devices.

The FIG. 4b illustrates a server 402 communicating with multiple electronic devices 404. The electronic device 404 can be a smart phone 404a, a laptop 404b, a computer 404c or a smart watch 404n. The server 402 is responsible for transmitting processed notification information to the electronic devices 404 through the transmitter. The transmitted information includes the information about the gases i.e. the concentration of the hazardous gases or the decrease in oxygen level. The transmitter information also includes live feed of the vitals of the laborers. This information contains a number of health parameters such as the blood pressure, heart rate, body temperature and the last time of movement of the laborers working inside the confined space. In addition to this, a video feed of the location is also provided by the server on a real-time basis. These visuals can be also be stored in the electronic for a later viewing.

Further, the cloud server can be connected with multiple other electronic devices at the same time such as a laptop, a tablet, a smartphone, or a desktop on a real-time basis as shown in FIG. 4b.

Figure 5:
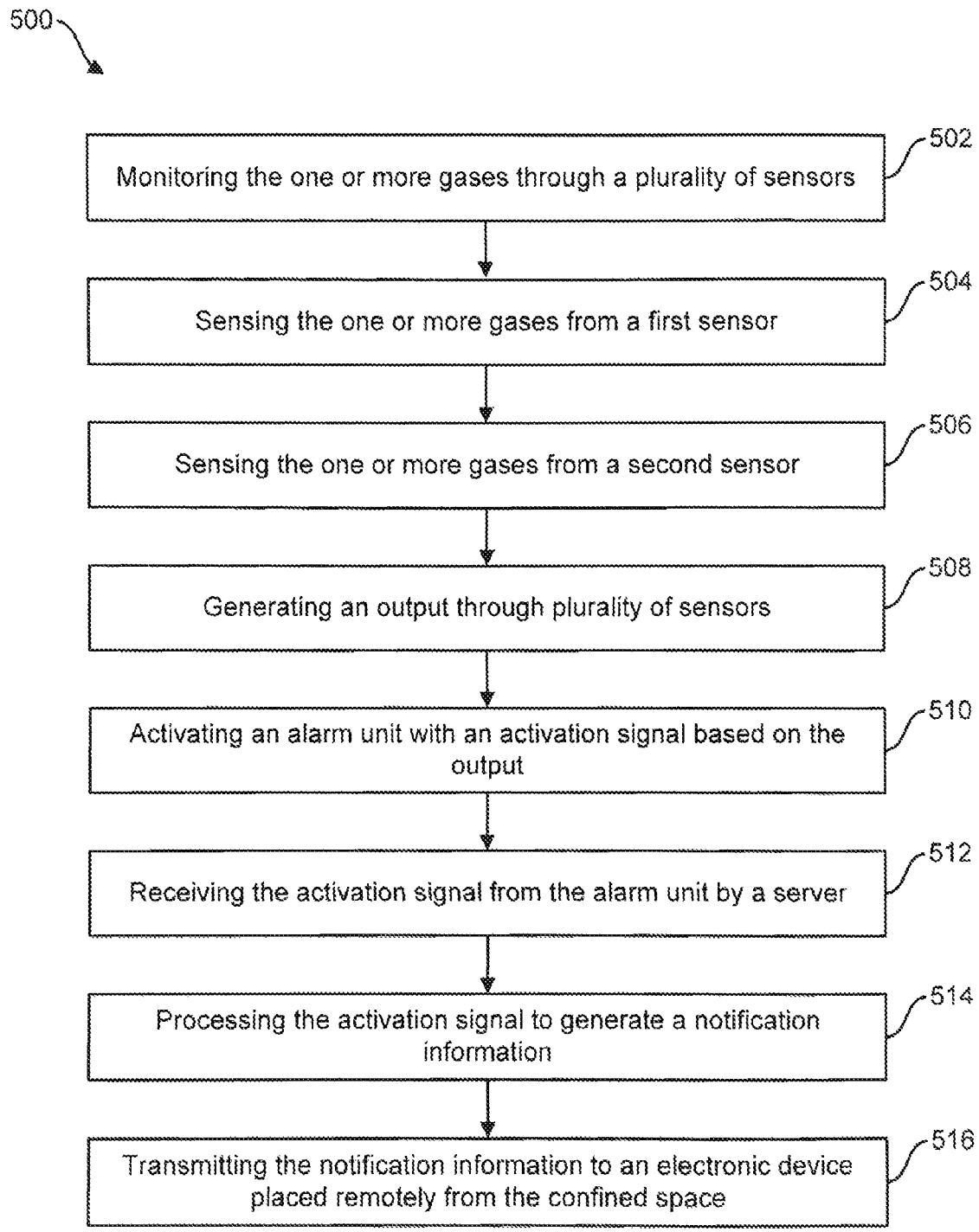
FIG. 5 Illustrate a method for monitoring presence of hazardous gases in a confined space.

FIG. 5 illustrates method for monitoring a confined space for the presence of hazardous gases in a confined space. The method includes measuring the concentration of one or more gases inside the confined space 502 with the help of a sensing unit configured within the housing that includes a plurality of sensors.

Sensing the concentration of one or more gases that first inlet provides to the first sensor 504. Similarly, sensing the concentration of one or more gases that second inlet provides to the second sensor 506. The first and the second sensor of steps 504 and 506 are capable of sensing an increase in the concentration of hazardous gases beyond a set threshold value and a drop in the level of oxygen below a certain point. In both of the above-mentioned cases, the multiple sensors generate output 508. The output is received by an alarm unit that further leads generating activation signal 510. The alarm unit includes a sound alarm and a flashlight. The activation signal is generated along with the activation of the sound alarm and turning on of the flashlight.

Further, the sent activation signal is received by the server 512. The server processes the received activation signal and generates a notification using the activation signal 514. The server also provides the live feed of the surroundings of the laborers present inside the confined space. Lastly, in step 516, the notification information that contains a variety of information such as the live feed, various health parameters of the laborers working inside the confined space etc. is transmitted to one or more electronic devices placed remotely from the confined space.

While, the various embodiments of the present invention have been described above, it should be understood that they have been presented by way of example only, and not of limitation. Likewise, the figure may depict an example architectural or other configuration for the invention, which is done to aid in understanding the features and functionality that can be included in the invention. The invention is not restricted to the illustrated example architectures or configurations, but the desired features can be implemented using a variety of alternative architecture and configurations.

Although, the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

The presence of broadening words and phrases such as "one or more," "at least," "but not limited to" or other like phrases in some instances shall not be read to mean that the narrower case is intended or required in instances where such broadening phrases may be absent.

The invention claimed is:

1. A gas monitoring device for monitoring one or more gases at a location, the gas monitoring device comprising:
an infrared camera positioned on a housing of the gas monitoring device, wherein the infrared camera records visual at the location;
a plurality of rechargeable batteries for powering the gas monitoring device;
a plurality of sensors, wherein the plurality of sensors include:
a first sensor coupled with an inlet port on the housing of the gas monitoring device, wherein the inlet port receives the one or more gases to be sensed by the first sensor to generate a first output; and
a second sensor coupled with an extension tube connected with the housing of the gas monitoring device, wherein the extension tube receives the one or more gases to be sensed by the second sensor to generate a second output;
an alarm unit connected with the plurality of sensors, wherein the alarm unit includes:
a flashlight, wherein the flashlight is activated based on either of the first output or the second output; and
an alarm, wherein the alarm is activated based on either of the first output or the second output.

2. The gas monitoring device according to claim 1, wherein the gas monitoring device includes a magnet for fixing the gas monitoring device with wall.

3. The gas monitoring device according to claim 1, where the plurality of rechargeable batteries further includes a power monitor and an LED.

4. The plurality of rechargeable batteries according to claim 3 are replaceable batteries.

5. The gas monitoring device according to claim 1, wherein the infrared camera is wirelessly connected with a display screen placed at another location.

6. The gas monitoring device according to claim 5, wherein the infrared camera is connected through a wire with the display screen placed at the another location.

7. The gas monitoring device according to claim 1, wherein the one or more gases are either of carbon monoxide, hydrogen disulfide and oxygen.

8. The gas monitoring device according to claim 7, wherein the first output and the second output is based on a pre-defined threshold value of each of the one or more gases.

9. The threshold value according to claim 8, wherein the pre-defined threshold value of each of the one or more gases is based on concentration of the one or more gases at the location.

10. The gas monitoring device according to claim 9, wherein the activation of either of the flashlight or the alarm is based on the pre-defined threshold value.

11. The gas monitoring device according to claim 1, wherein length of the extension tube is about 4 feet.

12. A system for notifying presence of one or more gases in a confined space, the system comprising:
a gas monitor for monitoring the one or more gases, the gas monitor further includes:
(a) a plurality of sensors, wherein the plurality of sensors comprises:
a first sensor coupled with an inlet port on a housing of the gas monitor, wherein the inlet port receives the one or more gases to be sensed by the first sensor to generate a first output;
a second sensor coupled with an extension tube connected with the housing of the gas monitor, wherein the extension tube receives the one or more gases to be sensed by the second sensor to generate a second output;
(b) an alarm unit connected with the plurality of sensors to receive the first output and the second output, wherein the alarm unit includes a flashlight and an alarm, further wherein each of the flashlight and the alarm are activated along with an activation signal based on either of the first output or the second output;
a server in communication with the gas monitor, wherein the server receives the activation signal from the alarm unit, the server comprising:
(a) a receiver for receiving the activation signal;
(b) a processor for processing the activation signal to generate a notification information;
(c) a transmitter for transmitting the notification information to one or more electronic devices.

13. The system according to claim 12, wherein the flashlight and the alarm are activated if concentration of the one or more gases sensed by the plurality of sensors is above threshold values.

14. The system according to claim 13, wherein the alarm unit generates the activation signal if concentration of the one or more gases sensed by the plurality of sensors is above the threshold values.

15. The system according to claim 14, wherein each of the one or more gases is associated with a threshold value.

16. The system according to claim 12, wherein the server is a cloud server.

17. The system according to claim 12, wherein the one or more electronic devices is either a smartwatch, a tablet, a desktop computer, a smart phone, or a laptop.

18. The system according to claim 12, wherein the one or more electronic devices include an interface for displaying the notification information.

19. The system according to claim 18, wherein the notification information is either of a graph, a text, an audio, or a multi-media message.

20. The system according to claim 17, wherein the one or more electronic devices are wearable electronic devices capable of monitoring healthcare parameters of professionals at the location based on the activation signal.

21. A gas monitoring device for monitoring one or more gases at a location, the gas monitoring device comprising:

a camera positioned on a housing of the gas monitoring device, wherein the camera records visual at the location;
a plurality of rechargeable batteries for powering the gas monitoring device;
a plurality of sensors, wherein the plurality of sensors include:
 a first sensor coupled with an inlet port on the housing of the gas monitoring device, wherein the inlet port receives the one or more gases to be sensed by the first sensor to generate a first output; and
 a second sensor coupled with an extension tube connected with the housing of the gas monitoring device, wherein the extension tube receives the one or more gases to be sensed by the second sensor to generate a second output;
an alarm unit connected with the plurality of sensors, wherein the alarm unit includes:
 a flashlight, wherein the flashlight is activated based on either of the first output or the second output; and
 an alarm, wherein the alarm is activated based on either of the first output or the second output;
wherein the camera is wirelessly connected with a display screen placed at another location; and
wherein the camera is connected through a wire with the display screen placed at the another location.

* * * * *